United States Patent [19]

Brown et al.

[11] 4,108,851

[45] Aug. 22, 1978

[54] 3β,17-DIHYDROXY-5α,17α-PREGN-20-ENE-21-CARBOXYLIC ACID γ-LACTONE AND ESTERS THEREOF

[75] Inventors: Edward A. Brown, Glenview; Frank B. Colton, Evanston, both of Ill.

[73] Assignee: G. D. Searle & Co., Chicago, Ill.

[21] Appl. No.: 817,318

[22] Filed: Jul. 20, 1977

[51] Int. Cl.$^2$ ............................................. C07J 71/00
[52] U.S. Cl. ...................... 260/239.57; 260/239.55 R; 260/397.5
[58] Field of Search .....................................
/Machine Searched Steroids

[56] References Cited

U.S. PATENT DOCUMENTS

| 3,595,883 | 7/1971 | Afonso | 260/239.57 |
| 4,057,543 | 11/1977 | Dryden, Jr. | 260/239.57 |

FOREIGN PATENT DOCUMENTS

| 1,369,958 | 8/1964 | France | 260/239.57 |
| 1,369,960 | 8/1964 | France | 260/239.57 |

*Primary Examiner*—Elbert L. Roberts
*Attorney, Agent, or Firm*—John M. Brown

[57] ABSTRACT

Preparation of 3β,17-dihydroxy-5α,17α-pregn-20-ene-21-carboxylic acid γ-lactone and esters thereof, the analgesic utility of the esters, and the utility of the diol both as an intermediate and by reason of its antiviral activity are disclosed.

3 Claims, No Drawings

3β,17-DIHYDROXY-5α,17α-PREGN-20-ENE-21-CARBOXYLIC ACID γ-LACTONE AND ESTERS THEREOF

This invention relates to 3β,17-dihydroxy-5α,17α-pregn-20-ene-21-carboxylic acid γ-lactone, its esters, and processes for the preparation thereof. More particularly, this invention provides new, useful, and unobvious chemical compounds of the formula

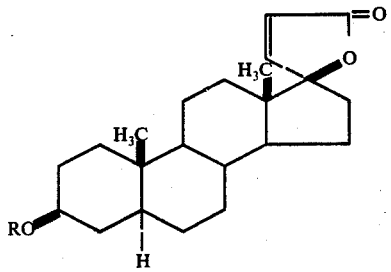

wherein R represents hydrogen or an acyl radical, the latter being preferably 1-oxoalkyl of the formula

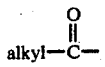

in which the alkyl grouping is methyl, ethyl, 1-methylethyl, 1,1-dimethylethyl, propyl, 1-methylpropyl, 2-methylpropyl, 2,2-dimethylpropyl, butyl, pentyl, 4-methylpentyl, hexyl, 3-methylhexyl, heptyl, or like monovalent, saturated, acyclic, straight- or branched-chain hydrocarbon moiety having the formula

wherein n represents a positive integer less than 8.

The esters to which this invention relates are useful as analgesics. Thus, for example, when tested by the standardized procedure for assaying analgesic activity described in U.S. Pat. No. 3,663,547, 3β-acetyloxy-17-hydroxy-5α, 17α-pregn-20-ene-21-carboxylic acid γ-lactone (the product of Example 1F hereinbelow) was found active at 50mg/kg.

The diol of this invention, 3β,17-dihydroxy-5α,17α-pregn-20-ene-21-carboxylic acid γ-lactone (described in Example 2A hereinbelow) is useful both as an intermediate to the aforesaid esters and by reason of its antiviral activity. When tested via a procedure substantially identical with that set forth in U.S. Pat. No. 3,845,038 for assaying the capacity to inhibit the growth of influenza type A virus (strain 575), the diol was found active at a concentration of approximately 16 mcgm/ml.

Unlike compounds superficially structurally related, the products of Examples 1F and 2A hereinbelow did not significantly alter the renal electrolyte effects of desoxycorticosterone acetate when assayed for such antimineralocorticoid activity at the customary screening dose of 2.4 mg subcutaneously via a procedure substantially identical with that described in U.S. Pat. No. 3,926,962, The activities hereinbefore specified are provided merely for purposes of illustration, and accordingly are not to be construed as either delimiting or exclusionary.

Preparation of the compounds of this invention proceeds by contacting 3,4-dihydro-2H-pyran with 2-propyn-1-ol in the presence of 4-methylbenzenesulfonic acid, using 1,1'-oxybisethane as solvent; warming the resultant tetrahydro (2-propynyloxy)-2H-pyran with bromoethylmagnesium in 1,1'-oxybisethane under nitrogen to obtain bromo{3-[(tetrahydro-2H-pyran-2-yl)oxy]-1-propynyl}magnesium; warming the latter magnesium compound in situ with a solution of 3β-hydroxy-5α-androstan-17-one in tetrahydrofuran; 3-esterifying the resultant 17-{3-[(tetrahydro-2H-pyran-2-yl)oxy]-1-propynyl}-5α-androstane-3β,17β-diol by contacting it with acetic acid anhydride in pyridine; cleaving the acyclic ether linkage in the 3β-acetyloxy-17-{3-[(tetrahydro-2H-pyran-2-yl)oxy]-1-propynyl}-5α-androstan-17β-ol thus obtained by heating the compound with dilute hydrochloric acid in methanol; converting the resultant 3β-acetyloxy-17-(3-hydroxy-1-propynyl)-5α-androstan-17β-ol to 3β-acetyloxy-17-(3-hydroxy-1-propenyl)-5α- androstan-17β-ol by contacting a solution of the propynyl compound in a mixture of pyridine and tetrahydrofuran with hydrogen at a pressure of 1.4 × $10^4$ N m$^{-2}$ in the presence of palladium on calcium carbonate catalyst; and oxidizing the primary hydroxyl in the propenyl compound to carboxyl by warming a 2-propanone solution of the compound with chromium oxide dissolved in aqueous sulfuric acid, under which conditions dehydration occurs and 3β-acetyloxy-17-hydroxy-5α,17α-pregn-20-ene-21-carboxylic acid γ-lactone eventuates. Upon heating 3β-acetyloxy-17-hydroxy-5α,17α-pregn-20-ene-21-carboxylic acid γ-lactone with potassium hydroxide in aqueous methanol and then acidifying, 3β,17β-dihydroxy-5α,17α-pregn-20-ene-21-carboxylic acid γ-lactone is obtained, which can be converted into the corresponding 3-acetate or any other ester of the invention by prolonged contact in pyridine with the appropriate alkanoic acid anhydride.

The following examples describe in detail compounds illustrative of the present invention and methods which have been devised for their preparation. It will be apparent to those skilled in the art that many modifications, both of materials and of methods, may be practiced without departing from the purpose and intent of this disclosure. Throughout the examples hereinafter set forth, temperatures are given in degrees centigrade and relative amounts of materials in parts by weight, except as otherwise noted.

EXAMPLE 1

A. To a solution of 672 parts of 2-propyn-1-ol and 7 parts of 4-methylbenzenesulfonic acid monohydrate in 1135 parts of 1,1'-oxybisethane is added, during 15 minutes with stirring, a solution of 1010 parts of 3,4-dihydro-2H-pyran in 1135 parts of 1,1'-oxybisethane. Stirring of the resultant mixture at 20°-25° is continued for 2 hours after the addition is complete, whereupon a solution of 7 parts of potassium hydroxide in 30 parts of water is mixed in. The mixture thus obtained is dried over anhydrous sodium sulfate, then distilled in vacuo. The fraction boiling at 43°-45°/13-26 N m$^{-2}$ is tetrahydro-2-(2-propynyloxy)-2H-pyran.

B. To a solution of 108 parts of tetrahydro-2-(2-propynyloxy)-2H-pyran in 210 parts of 1,1'-oxybisethane at the boiling point under reflux in a nitrogen atmosphere is added, with stirring during 20 minutes, a solution of 98 parts of bromoethylmagnesium in approximately 700 parts of 1,1'-oxybisethane. Stirring at the boiling point under reflux is continued for 20 minutes after the addition is complete, at which point heating is discontinued and a solution of 50 parts of 3β-hydroxy-5α-androstan-17-one in approximately 225 parts of tetrahydrofuran is stirred in during 15 minutes. The mixture thus obtained is heated at the boiling point under reflux with stirring for 7 hours, then cooled to room temperature and consecutively diluted thereat with 50 parts of a saturated aqueous solution of ammonium chloride and 250 parts of water. The resultant mixture is filtered, whereupon the organic phase is separated, washed with water, dried over anhydrous sodium sulfate, and stripped of solvent by vacuum distillation. The residue is 17-{3-[(tetrahydro-2H-pyran-2-yl)oxy]-1-propynyl}-5α-androstane-3β,17β-diol.

C. A solution of 50 parts of 17-{3-[(tetrahydro-2H-pyran-2-yl)oxy]-1-propynyl}-5α-androstane-3β,17β-diol in a mixture of 300 parts of acetic anhydride and 500 parts of pyridine is maintained at room temperatures for 24 hours, then poured into 4000 parts of ice-water. The oily phase is extracted with 1,1'-oxybisethane. The extract is washed with water, dried over anhydrous sodium sulfate, and stripped of solvent by vacuum distillation. The oily residue is 3β-acetyloxy-17-{3-[(tetrahydro-2H-pyran-2-yl)oxy]-1-propynyl}-5α-androstan-17β-ol.

D. A solution of 50 parts of 3β-acetyloxy-17-{3-[(tetrahydro-2H-pyran-2-yl)oxy]-1-propynyl}-5αandrostan-17β-ol, 14 parts of concentrated hydrochloric acid, and 24 parts of water in 395 parts of methanol is heated to the boiling point, then cooled to approximately 25° during 2 hours. The resultant solution is diluted with 3 volumes of water. The mixture thus obtained is cooled to 5°, whereupon insoluble solids are isolated by filtration, washed with water, dried in air, and recrystallized from ethyl acetate. The product thus obtained is 3β-acetyloxy17-(3-hydroxy-1-propynyl)-5α-androstan-17β-ol melting in the range 180°–190°.

E. A solution of 10 parts of 3β-acetyloxy-17-(3-hydroxy-1-propynyl)-5α-androstan-17β-ol in a mixture of approximately 20 parts of pyridine with 150 parts of tetrahydrofuran is hydrogenated at a pressure of 1.4 × $10^4$ N m$^{-2}$ and a temperature of around 25° in the presence of 1 part of palladium on calcium carbonate catalyst. After approximately 20 minutes, hydrogen uptake indicates that the desired reduction is complete, whereupon catalyst is filtered out and the filtrate stripped of solvent by vacuum distillation. The residue, twice recrystallized from ethyl acetate, affords 3β-acetyloxy-17-(3-hydroxy-1-propenyl)-5α-androstan-17β-ol melting in the range 150°–160°.

F. To a solution of 12 parts of 3β-acetyloxy-17-(3-hydroxy-1propenyl)-5α-androstan-17β-ol in 330 parts of 2-propanone is added, with stirring during 30 minutes at temperatures not to exceed 35°, 46 parts of a solution of chromium oxide in aqueous sulfuric acid prepared by dissolving 10 parts of chromium oxide in 20 parts of water and consecutively adding thereto 15 parts of concentrated sulfuric acid and 20 parts of water. Stirring is continued for 30 minutes after the addition is complete, at which point 4 parts of 2-propanol followed by just sufficient water to produce a clear green solution is stirred in. The resultant mixture is poured into approximately 2500 parts of cold water. The precipitate which forms is isolated by filtration, washed with water, dried in air, and recrystallized from ethyl acetate. The product is 3β-acetyloxy-17 -hydroxy-5α,17α-pregn-20-ene-21-carboxylic acid γ-lactone melting at 181°–189°. It has the formula

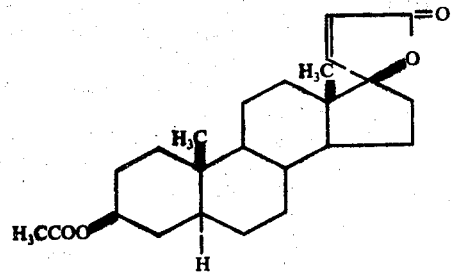

Example 2

A. To a solution of 34 parts of 3β-acetyloxy-17-hydroxy-5α,17α-pregn-20-ene-21carboxylic acid γ-lactone in 395 parts of methanol is added a solution of 10 parts of potassium hydroxide in 50 parts of water. The resultant mixture is heated at the boiling point under reflux for 30 minutes, then cooled to room temperature and thereupon acidified with 20% hydrochloric acid. The resultant mixture is maintained at room temperature for 30 minutes during which a precipitate forms, then poured into 3000 parts of cold water. Insoluble solids are isolated by filtration, washed with water, dried in air, and recrystallized from ethyl acetate to give 3β,17-dihydroxy-5α,17α-pregn-20-ene-21-carboxylic acid γ-lactone melting at 169°–179°.

B. A solution of 1 part of 3β,17-dihydroxy-5α,17α-pregn-20-ene-21-carboxylic acid γ-lactone in a mixture of 10 parts of propanoic acid anhydride and 10 parts of pyridine is maintained at room temperature for 18 hours, then poured into 100 parts of ice-water. The insoluble solids which precipitate are filtered off, washed with water, and dried in air. The product thus isolated, 17-hydroxy-3β-[(1-oxopropyl)oxy]-5α,17α-pregn-20-ene-21-carboxylic acid γ-lactone, can be further purified by recrystallization from ethyl acetate. The product has the formula

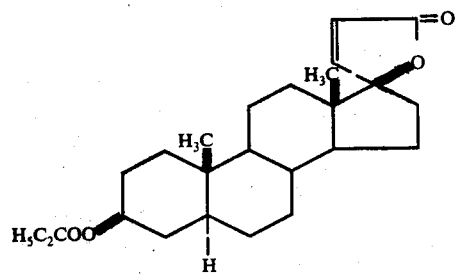

What is claimed is:
1. A compound of the formula

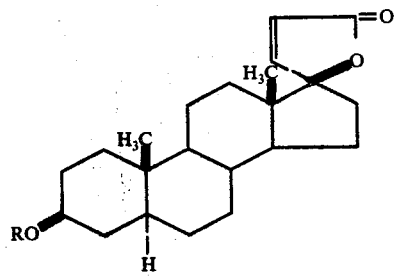

wherein R represents 1-oxoalkyl containing fewer than 9 carbons.

2. A compound according to claim 1 which is 3β-acetyloxy-17-hydroxy-5α,17α-pregn-20-ene-21-carboxylic acid γ-lactone.

3. 3β,17-dihydroxy-5α,17α-pregn-20-ene-21-carboxylic acid γ-lactone.

* * * * *